United States Patent [19]

Rosenberger et al.

[11] 4,069,197
[45] Jan. 17, 1978

[54] DIONES AND THEIR USE AS POLYMER STABILIZERS

[75] Inventors: Siegfried Rosenberger, Riehen; Andreas Schmidt, Reinach, both of Switzerland

[73] Assignee: Ciba-Geigy Corporation, Ardsley, N.Y.

[21] Appl. No.: 672,566

[22] Filed: Mar. 31, 1976

[30] Foreign Application Priority Data

Apr. 10, 1975 Switzerland ............... 4568/75

[51] Int. Cl.² .................. C07D 233/72; C08K 5/34
[52] U.S. Cl. ............. 260/45.8 NE; 260/45.7 PH; 260/45.8 R; 260/45.8 NT; 548/335
[58] Field of Search ............ 260/45.8 NB, 309.5

[56] References Cited
U.S. PATENT DOCUMENTS

| | | | |
|---|---|---|---|
| B 532,140 | 3/1976 | Dexter et al. | 260/473 S |
| 3,821,161 | 6/1974 | Stephen | 260/45.8 NB |
| 3,821,162 | 6/1974 | Dexter | 260/45.8 NB |
| 3,919,234 | 11/1975 | Ramey et al. | 260/45.8 NB |
| 3,939,175 | 2/1976 | Schmidt et al. | 260/309.5 |
| 3,971,803 | 7/1976 | Rosenberger et al. | 260/307 A |

Primary Examiner—Donald E. Czaja
Assistant Examiner—R. A. White
Attorney, Agent, or Firm—Nestor W. Shust

[57] ABSTRACT

Compounds of the formula I

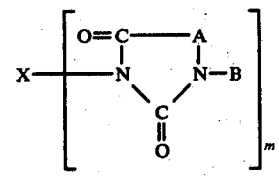

wherein A is alkylidene or optionally alkylated vinylene, B is a group of the formula II

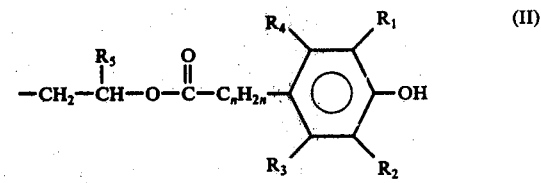

wherein $R_1$ and $R_2$ are alkyl, $R_3$, $R_4$ and $R_5$ are hydrogen or alkyl and $n$ is 0, 1 or 2 and $m$ is 1 or 2, and X is identical to B if $m$ equals 1 or X is methylene if $m$ equals 2, as stabilisers for organic material.

9 Claims, No Drawings

DIONES AND THEIR USE AS POLYMER STABILIZERS

The present invention relates to N-heterocyclic compounds, their manufacture, their use for stabilising organic material and the organic material stabilised with the aid of these compounds.

It is known to employ derivatives of sterically hindered phenols as stabilisers, for organic polymers, against thermo-oxidative degradation of the polymers or against light ageing of the polymers. Many of these phenol derivatives have the disadvantage of objectionably discolouring the organic polymer, either already during their incorporation or by the action of light or on contact with industrial waste gases or also on contact with hot water, which greatly limits their industrial applicability. n-Octadecyl β-(3,5-di-tert.-butyl-4-hydroxyphenyl)-propionate, for example, which is structurally related to the new compounds, is known and commercially available; compare British patent specification No. 990,304. New compounds have now been found which, surprisingly, are not only outstandingly suitable for stabilising organic materials, in particular organic polymers, but also, at the same time, remain colourless under the conditions mentioned and protect the organic material against discolouration for a long time. This means that the new compounds stabilise the organic material both against degradation and against discolouration.

The invention thus relates to compounds of the formula I

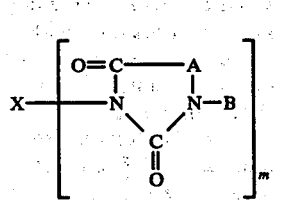

wherein A is alkylidene or optionally alkylated vinylene, B is a group of the formula II

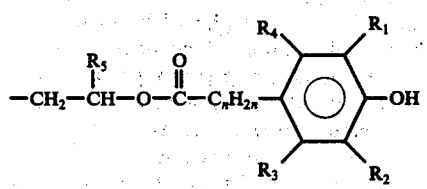

wherein $R_1$ and $R_2$ are alkyl, $R_3$, $R_4$ and $R_5$ are hydrogen or alkyl and $n$ is 0, 1 or 2 and $m$ is 1 or 2, and X is identical to B if $m$ equals 1 or X is methylene if $m$ equals 2.

A as alkylidene is, for example, methylene which is optionally substituted by one or two alkyl groups, in particular with 1-24 C atoms, above all methylene substituted by one or, in particular two, alkyl groups with 1-6 C atoms, such as, above all, isopropylidene or ethylidene. A as optionally alkylated vinylene is vinylene which is substituted, in particular, by alkyl with 1-12 C atoms, the alkyl substituent being, in particular, adjacent to a ring N atom, for example vinylene which is substituted by alkyl with 1-6 C atoms, such as, in particular, methylvinylene.

$R_1$ and $R_2$ as alkyl are, for example, independently of one another, straight-chain or branched alkyl with 1-12 C atoms, in particular 1-8 C atoms, such as methyl, ethyl, n-propyl, iso-propyl, n-butyl, sec.-butyl, tert.-butyl, 2-ethylbutyl and n-octyl. α-Branched alkyl radicals with 3-8 C atoms, in particular tert.-butyl, are preferred.

$R_3$, $R_4$ and $R_5$ as alkyl are, for example, independently of one another, straight-chain or branched alkyl with 1-12 C atoms, in particular 1-8, and above all 1-4. In particular, methyl is suitable. However, $R_3$, $R_4$ and $R_5$ are, above all, hydrogen.

Compounds of the formula I, wherein A is alkylidene with 1-13 C atoms or vinylene which is optionally substituted with alkyl with 1-6 C atoms, adjacent to the ring N atom, $R_1$ and $R_2$ are alkyl with 1-8 C atoms, $R_3$, $R_4$ and $R_5$ are hydrogen, $n$ is 0, 1 or 2, $m$ is 1 or 2 and X is identical to B if $m$ equals 1 or X is methylene if $m$ equals 2, are preferred.

Compounds of the formula I, wherein A is isopropylidene, ethylidene or methylvinylene, in which the methyl substituent is adjacent to the ring N atom, $R_1$ and $R_2$ are α-branched alkyl with 3-8 C atoms, $R_3$, $R_4$ and $R_5$ are hydrogen, $n$ is 0, 1 or 2, $m$ is 1 or 2 and X is identical to B if $m$ equals 1 or X is methylene if $m$ equals 2, are particularly preferred.

In the preferred compounds of the formula I, $R_1$ and $R_2$ are, in particular, tert.-butyl.

In the preferred compounds of the formula I, $n$ is, in particular, 2.

Examples which may be mentioned are:
1. 1,1'-Methylene-bis[3-[3-(3,5-di-tert.-butyl-4-hydroxyphenyl)-propionyl-oxyethyl]-5,5-dimethyl-hydantoin].
2. 1,3-Di-[3-3,5-di-tert.-butyl-4-hydroxyphenyl)-propionyl-oxyethyl]-5,5-dimethylhydantoin.
3. 1,3-Di-[3-(3,5-di-tert.-butyl-4-hydroxyphenyl)-propionyl-oxyethyl]-6-methyl-1,2,3,4-tetrahydro-pyrimidine-2,4-dione.

The compounds of the formula I can be manufactured by methods which are in themselves known.

For example, the procedure followed can be to react an acid of the formula II

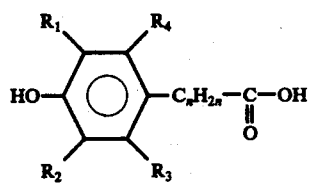

wherein $R_1$, $R_2$, $R_3$, $R_4$ and $n$ have the above meaning, or a reactive derivative thereof, with an alcohol of the formula III

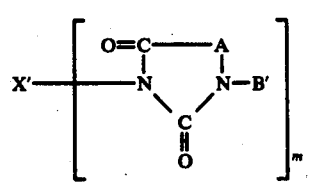

wherein A has the above meaning, B' is a radical —CH$_2$—CH(R$_5$)OH, $m$ is 1 or 2 and X' is identical to B' if $m$ equals 1 or X' is methylene if $m$ equals 2.

A reactive derivative of an acid of the formula II is, for example, an ester, in particular an alkyl ester with preferably 1–6 C atoms, such as the methyl ester, an anhydride, for example a mixed anhydride or, in particular, an anhydride of two mols of an acid of the formula II, and a halide, for example a chloride.

In the case of an ester the reaction is suitably carried out in the presence of catalytic amounts of a base, such as inorganic bases, for example oxides, alkoxides, hydroxides and amides of alkali metals and alkaline earth metals, such as sodium methylate, sodium hydroxide, potassium hydroxide and sodium amide. Preferably, about 2 mols of ester per mol of alcohol are used.

In the case of a halide the reaction is preferably carried out in the presence of an acid-binding agent, such as an organic or inorganic base, for example a tertiary amine, such as trimethylamine and triethylamine, or an alkali metal hydroxide, such as sodium hydroxide or potassium hydroxide. About 2 mols of acid-binding agent and about 2 mols of halide are suitably used per mol of alcohol. Solvents are advantageously used for the reaction, for example amides, such as dimethylformamide and dimethylacetamide, aromatic hydrocarbons, such as benzene and toluene, or ethers, such as diethyl ether and tetrahydrofurane.

If the free acid of the formula II is used, the reaction is advantageously carried out in the presence of an acid catalyst, such as a strong acid, for example hydrochloric acid, sulphuric acid or a sulphonic acid, such as p-toluenesulphonic acid. The water formed during the esterification is removed in a suitable manner, for example by azeotropic distillation or by adding a water-binding agent, for example phosphorus pentoxide or a carbodiimide. In particular, about 2 mols of acid of the formula II are used per mol of alcohol.

The starting materials are known or, if they are new, can be manufactured analogously to the manufacture of known compounds by methods which are in themselves known. Thus acids or esters of the formula II are known, for example from British patent specification No. 990,304, or, if they are new, can be manufactured analogously to the previously known methods. Other reactive derivatives of the acids of the formula II can be manufactured from the acids in a known manner, for example anhydrides by means of dehydrating agents, such as phosphorus pentoxide, and halides by means of halogenating agents, such as phosphorus oxyhalides, for example phosphorus oxychloride, or sulphuryl halides, such as sulphuryl chloride. The alcohols of the formula III are known and can be obtained, for example, in the customary manner from the corresponding NH compounds with, for example, $R_5$-substituted ethylene oxide.

According to the present invention, the compounds of the formula I can be used as stabilisers for organic substrates. Examples of possible substrates are:

1. Polymers which are derived from hydrocarbons with single or double unsaturation, such as polyolefines, for example polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylenepropylene copolymers, propylene-butene-1 copolymers, propyleneisobutylene copolymers, styrene-butadiene copolymers and terpolymers of ethylene and propylene with a diene, such as, for example, hexadiene, dicyclopentadiene or ethylidenenorbornene; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, and polyvinyl fluoride, but also polychloroprene and chlorinated rubbers.

3. Polymers which are derived from $\alpha,\beta$-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as a comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerol-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers, such as cellulose, rubber, proteins and their polymer-homologously chemically modified derivatives, such as cellulose acetates, cellulose propionates and cellulose butyrates, or the cellulose ethers, such as methylcellulose.

17. High molecular monomeric substances, for example mineral oils, animal and vegetable fats, oils and waxes, or oils, waxes and fats based on synthetic esters.

The use of the compounds of the formula I for stabilising homopolymers and copolymers of olefines, such as the substrates mentioned under 1, and of polyamides and polyurethanes is of particular importance.

The compounds of the formula I are generally incorporated into the substrates in a concentration of 0.01 to 5% by weight, calculated relative to the material to be stabilised. Preferably, 0.05 to 2.0, and particularly preferentially 0.1 to 1.0% by weight of the compounds, calculated relative to the material to be stabilised, are incorporated into the latter. The incorporation can take place, for example, by mixing in at least one of the compounds of the formula I and optionally further additives according to the methods customary in the art, before or during shaping, or by applying the dissolved or dispersed compounds to the polymer, if appropriate with subsequent evaporation of the solvent.

In the case of crosslinked polyethylene, the compounds of the formula I are appropriately added before crosslinking. The compounds of the formula I can also be added before or during the polymerisation.

As further additives, together with which the stabilisers according to the invention can be employed, there should be mentioned:

1. Antioxidants of the aminoaryl and hydroxyaryl series.

In the case of the latter, the sterically hindered phenol compounds of the following classes should be mentioned:

1.1. Simple 2,6-dialkylphenols, such as, for example, 2,6-di-tert.butyl-4-methylphenol, 2-tert.butyl-4,6-dimethylphenol, 2,6-di-tert.butyl-4-methoxymethylphenol and 2,6-dioctadecyl-4-methylphenol.

1.2. Derivatives of alkylated hydroquinones, such as, for example, 2,5-di-tert.butyl-hydroquinone, 2,5-di-tert.amyl-hydroquinone, 2,6-di-tert.butyl-hydroquinone, 2,5-di-tert.butyl-4-hydroxy-anisole, 3,5-di-tert.butyl-4-hydroxy-anisole and tris-(3,5-di-tert.butyl-4-hydroxyphenyl) phosphite.

1.3. Hydroxylated thiodiphenyl ethers, such as, for example, 2,2'-thio-bis-(6-tert.butyl-4-methylphenol), 2,2'-thio-bis-(4-octylphenol), 4,4'-thio-bis-(6-tert.butyl-3-methylphenol), 4,4'-thio-bis-(3,6-di-sec.amylphenol) and 4,4'-thio-bis-(6-tert.butyl-2-methylphenol).

1.4. Alkylidene-bisphenols, such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-di-tert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.butyl-4-hydroxy-2-methylphenyl)-pentane and ethylene glycol bis-[3,5-bis-(3'-tert.butyl-4'-hydroxyphenyl)-butyrate].

1.5. O-, N- and S-benzyl compounds, such as, for example, 3,5,3',5'-tetra-tert-butyl-4,4'-dihydroxydibenzyl ether, 4-hydroxy-3,5-dimethylbenzyl-mercaptoacetic acid octadecyl ester, tri-(3,5-di-tert.butyl-4-hydroxybenzyl)-amine and bis-(4-tert.butyl-3-hydroxy-2,6-dimethylbenzyl)-dithiol terephthalate.

1.6. Hydroxybenzylated malonic esters, such as, for example, 2,2-bis-(3,5-di-tert.butyl-4-hydroxybenzyl)-malonic acid diotadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid didodecylmercaptoethyl ester and 2,2-bis-(3,5-di-tert.butyl-4-hydroxybenzyl) malonic acid di-(4-tert.octylphenyl) ester.

1.7 Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8. s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxyphenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9. Amides of 3,5-di-tert.butyl-4-hydroxyphenyl-propionic acid, such as, for example, 1,3,3-tri-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10. Esters of 3,5-di-tert.butyl-4-hydroxyphenyl-propionic acid with monohydric or polyhydric alcohols, such as, for example, with methanol, ethanol, octadecanol, 1,6-hexanediol, 1,4-nonanediol, ethylene glycol, 1,2-propanediol, diethylene glycol, thiodiethylene glycol, neopentyl glycol, 3-thiaundecanol, 3-thiapentadecanol, trimethylhexanediol, trimethylolethane, trimethylolpropane, pentaerythritol, tris-hydroxyethylisocyanurate and 4-hydroxymethyl-1-phospha-2,6,7-trioxabicyclo[2,2,2]octane.

1.11. Esters of 5-tert.butyl-4-hydroxy-3-methylphenylpropionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, 3-thiaundecanol, 3-thiapentadecanol, trimethylhexanediol, trimethylolethane, trimethylolpropane, pentaerythritol, trishydroxyethyl-isocyanurate and 4-hydroxymethyl-1-phospha-2,6,7-trioxabicyclo[2,2,2]octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, 3-thiaundecanol, 3-thiapentadecanol, trimethylhexanediol, trimethylolethane, trimethylolpropane, pentaerythritol, tris-hydroxyethylisocyanurate and 4-hydroxymethyl-1-phospha-2,6,7-trioxabicyclo[2,2,2]octane.

1.13. Acylaminophenols, such as, for example, N-(3,5-di-tert.butyl-4-hydroxyphenyl)-stearic acid amide and N,N'-di-(3,5-di-tert.butyl-4-hydroxyphenyl)-thio-bis-acetamide.

1.14. Benzylphosphonates, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

2. UV absorbers and light stabilisers, such as:
2.1. 2-(2'-Hydroxyphenyl)-benztriazoles, for example the 5'-methyl-, 3',5'-di-tert.butyl-, 5'-tert.butyl-, 5-chloro-3',5'-di-tert.butyl-, 5'-chloro-3'-tert.butyl-5'-methyl-, 3'-sec. butyl-5'-tert.butyl-, 3'-[α-methylbenzyl]-5'-methyl-, 3'-[α-methylbenzyl]-5'-methyl-5-chloro-, 4'-octoxy-, 3',5'-di-tert.amyl-, 3'-methyl-5'-carbomethoxyethyl- and 5-chloro-3',5'-di-tert.amyl-derivative.
2.2. 2,4-Bis-(2'-hydroxyphenyl)-6-alkyl-s-triazines, for example the 6-ethyl- or 6-undecyl- derivative.
2.3. 2-Hydroxy-benzophenones, for example the 4-hydroxy-, 4-methoxy-, 4-octoxy-, 4-decyloxy-, 4-dodecyloxy-, 4,2',4'-trihydroxy- or 2'-hydroxy-4,4'-dimethoxy- derivative.
2.4. 1,3-Bis-(2'-hydroxybenzoyl)-benzenes, for example 1,3-bis-(2'-hydroxy-4'-hexyloxy-benzoyl)-benzene, 1,3-bis-(2'-hydroxy-4'-octoxy-benzoyl)-benzene and 1,3-bis-(2'-hydroxy-4'-dodecyloxy-benzoyl)-benzene.
2.5. Aryl esters of optionally substituted benzoic acids, such as, for example, phenyl salicylate, octylphenyl salicylate, dibenzoylresorcinol, bis-(4-tert.butylbenzoyl)-resorcinol, benzoylresorcinol and 3,5-di-tert. butyl-4-hydroxybenzoic acid 2,4-di-tert.butyl-phenyl ester or octadecyl ester or 2-methyl-4,6-di-tert.butyl-phenyl ester.
2.6. Acrylates, for example α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methylindoline.
2.7. Nickel compounds, for example nickel complexes of 2,2'-thio-bis-(4-tert.octylphenol), such as the 1:1 and 1:2 complex, optionally with other ligands, such as n-butylamine, nickel complexes of bis-(4-tert.octylphenol)-sulphone, such as the 2:1 complex, optionally with other ligands, such as 2-ethylcaproic acid, nickel dibutyldithiocarbamate, nickel salts of 4-hydroxy-3,5-di-tert.butylbenzyl-phosphonic acid monoalkyl esters, such as the methyl, ethyl or butyl ester, the nickel complex of 2-hydroxy-4methyl-phenyl-undecylketoxime.
2.8. Oxalic acid diamides, for example 4,4'-di-octyloxyoxanilide, 2,2'-di-octyloxy-5,5'-di-tert.butyl-oxanilide and 2,2'-di-dodecyloxy-5,5'-di-tert.butyl-oxanilide.
2.9. 2,2,6,6-Tetramethylpiperidines, such as 2,2,6,6-tetramethyl-4-stearoyloxypiperidine and bis-(2,2,6,6-tetramethyl-4-hydroxypiperidine)-sebacate.
3. Phosphites, such as triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetraoxa-3,9-diphosphaspiro[5,5]-undecane and tri-(4-hydroxy-3,5-di-tert.butylphenyl) phosphite.
4. Compounds which destroy peroxide, such as esters of β-thiodipropionic acid, for example the lauryl, stearyl, myristyl or tridecyl ester, salts of 2-mercaptobenzimidazole, for example the zinc salt, and diphenylthiourea.
5. Specific polyamide stabilisers, such as copper salts in combination with iodides and/or further phosphorus compounds and salts of divalent manganese.
6. Basic co-stabilisers, such as polyvinylpyrrolidone, melamine, benzoguanamine, triallyl cyanurate, dicyandiamide, urea derivatives, hydrazine derivatives, amines, polyamides, polyurethanes, and alkali metal salts and alkaline earth metal salts of higher saturated or unsaturated fatty acids, such as, for example, the laurates, myristates, palmitates, stearates, oleates or ricinoleates of calcium, magnesium, zinc, sodium or potassium. These salts are advantageously added, in concentrations of 0.1–40% by weight, preferably 1–10% by weight, to the stabiliser according to the invention before being incorporated into the material to be stabilised.
7. Specific PVC stabilisers, such as organic tin compounds, organic lead compounds and Ba/Cd salts of fatty acids.
8. Nucleating agents, such as 4-tert.butyl-benzoic acid, adipic acid and diphenylacetic acid.
9. Other additives, such as plasticisers, lubricants, for example glycerol monostearate, emulsifiers, antistatic agents, flameproofing agents, pigments, carbon black, asbestos, glass fibres, kaolin and talc.

The invention is described in more detail in the examples which follow. Percentages (%) therein denote percentages by weight and parts denote parts by weight. The temperatures are indicated in degrees Centigrade.

EXAMPLE 1

6.42 g (0.018 mol) of 1,1'-methylene-bis-[3-(3-hydroxyethyl)-5,5-dimethyl]-hydantoin, 10 g (0.036 mol) of 3-(3,5-di-tert.butyl-4-hydroxyphenyl)-propionic acid and 1 g of p-toluenesulphonic acid are first introduced into 100 ml of toluene and the mixture is heated for 1 hour under reflux under a water separator, whilst stirring. The mixture is then neutralised with sodium acetate and extracted with water and the organic phase is completely concentrated under reduced pressure. The residue is recrystallised from methanol. The 1,1'-methylene-bis-[3-[3-(3,5-di-tert.butyl-4-hydroxyphenyl)-propionyl-oxyethyl]-5,5-dimethylhydantoin] thus obtained melts at 148° C, Stabiliser No. 1.

If the 1,1'-methylene-bis-[3-(2-hydroxyethyl)-5,5-dimethyl]-hydantoin in this example is replaced by an equimolar amount of 1,3-di-(2-hydroxyethyl)-5,5-dimethyl-hydantoin or 1,3-di-(2-hydroxyethyl)-6-methyl-1,2,3,4-tetrahydropyrimidine -2,4-dione and the procedure followed is otherwise identical, 1,3-di-[3-(3,5-di-tert.-butyl-4-hydroxyphenyl)-propionyl-oxyethyl]-5,5-dimethyl-hydantoin, Stabiliser No. 2, or 1,3-di-[3-(3,5-di-tert.-butyl-4-hydroxyphenyl)-propionyl-oxyethyl]-6-methyl-1,2,3,4-tetrahydro-pyrimidine-2,4-dione, Stabiliser No. 3, is obtained.

These compounds are obtained as viscous, light brown oils and can be further purified by column chromatography.

EXAMPLE 2

100 Parts of polypropylene (melt index 2.6 g/10 minutes, 230° C/2,160 g) are intensively mixed for 10 minutes in a shaking apparatus with 0.2 part of one of the additives listed in Table 1 which follows.

The resulting mixture is kneaded in a Brabender plastograph for 10° minutes at 200° and the mass obtained in this way is subsequently pressed in a sheet press at 260° platen temperature to give 1 mm thick sheets, from which strips 1 cm wide and 17 cm long are punched.

The activity of the additives incorporated into the test strips is tested by heat ageing in a circulating air oven at 135° and 149°, with an additive-free test strip serving for comparison. Three test strips of each formulation are employed for the test. The end point is defined as the incipient decomposition of the test strip, which can be easily recognised by complete embrittlement. The results are indicated in days.

Table 1

| Stabiliser No. | Days to reach incipient decomposition at | |
|---|---|---|
| | 135° | 149° |
| without additive | 1 | <1 |
| 2 | 157 | 45 |
| 1 | 142 | 40 |
| 3 | 133 | 32 |

EXAMPLE 3

The test specimens described in Example 2 are furthermore tested for their colour stability, namely:
a. after incorporation (Table 2, column 2),
b. after 500 hours exposure in a Xenotest apparatus, by Messrs. Hanau (Table 2, column 3), and
c. after treatment with boiling water for 1 week (Table 2, column 4).

An empirical colour scale in which 5 denotes colourlessness, 4 denotes a slight discoloration which is just perceptible and 3, 2, 1 and <1 denote a successively increasing discoloration is used for the assessment.

Table 2

| Stabiliser No. | Colour assessment according to the scale 1-5 | | |
|---|---|---|---|
| | after incorporation | after exposure | boiling water for 1 week |
| without additive | 5 | 5 | 4-5 |
| 2 | 4-5 | 5 | 4-5 |
| 1 | 5 | 5 | 4-5 |
| 3 | 4-5 | 5 | 4-5 |

EXAMPLE 4

Assessment of the Resistance to "Gas Fading"

A piece of cotton fabric is soaked with a 1% strength solution of an additive of the Table 3 below, and is then dried. The piece of fabric treated in this way is exposed, in a closed chamber, to the off-gases of a row of natural gas burners at a temperature of 100° for 1 hour. The piece of fabric is then extracted with a mixture of 100 ml of dimethylacetamide and 1 ml of piperidine. The intensity of the coloration (usually yellow) of the resulting solution is considered a measure of the resistance to gas fading of the additive investigated.

An empirical colour scale in which 5 denotes colourlessness, that is to say very good resistance to gas fading, 4 denotes a slight discoloration which is just perceptible and 3, 2 and 1 denote a successively increasing discoloration was used for the Table 3.

Table 3

| Stabiliser No. | Colour assessment according to the scale 1-5, after gas fading |
|---|---|
| 1 | 4-5 |
| 3 | 4-5 |

What we claim is:
1. A compound of the formula

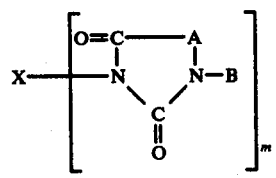

wherein A is alkylidene, B is a group of the formula

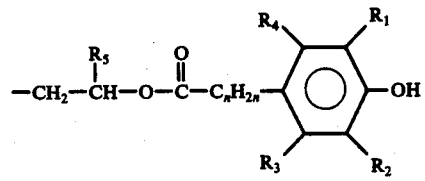

wherein $R_1$ and $R_2$ are alkyl, $R_3$, $R_4$ and $R_5$ are hydrogen or alkyl and $n$ is 0, 1 or 2 and $m$ is 1 or 2, and X is identical to B if $m$ equals 1 or X is methylene if $m$ equals 2.

2. A compound according to claim 1, wherein A is alkylidene with 1-13 C atoms, $R_1$ and $R_2$ are alkyl with 1-8 C atoms, $R_3$, $R_4$ and $R_5$ are hydrogen, $n$ is 0, 1 or 2, $m$ is 1 or 2 and X is identical to B if $m$ equals 1 or X is methylene if $m$ equals 2.

3. A compound according to claim 1, wherein A is isopropylicene, or ethylidene, $R_1$ and $R_2$ are α-branched alkyl with 3-8 C atoms, $R_3$, $R_4$ and $R_5$ are hydrogen, $n$ is 0, 1 or 2, $m$ is 1 or 2 and X is identical to B if $m$ equals 1 or X is methylene if $m$ equals 2.

4. A compound according to claim 1, wherein $n$ is 2.

5. The compound according to claim 1, which is 1,3-di-[3-(3,5-di-tert.butyl-4-hydroxyphenyl)-propionyl-oxyethyl]-5,5-dimethyl-hydantoin.

6. The compound according to claim 1, which is 1,1'-methylene-bis-[3-[3-(3,5-di-tert.-butyl-4-hydroxyphenyl)-propionyl-oxyethyl]-5,5-dimethyl-hydantoin].

7. A composition of matter comprising a synthetic organic polymer and from 0.01 to 5% by weight of a stabilizing compound of claim 1.

8. A composition of claim 7 wherein the organic material is polyolefine.

9. A composition of claim 8 wherein polyolefin is polypropylene.

* * * * *